(12) United States Patent
Mitts

(10) Patent No.: US 9,867,731 B2
(45) Date of Patent: Jan. 16, 2018

(54) URINE COLLECTION BAG ASSEMBLY

(71) Applicant: Cheryl Mitts, Las Vegas, NV (US)

(72) Inventor: Cheryl Mitts, Las Vegas, NV (US)

( * ) Notice: Subject to any disclaimer, the term of this patent is extended or adjusted under 35 U.S.C. 154(b) by 0 days.

(21) Appl. No.: 15/429,048

(22) Filed: Feb. 9, 2017

(65) Prior Publication Data

US 2017/0319373 A1 Nov. 9, 2017

Related U.S. Application Data

(60) Provisional application No. 62/331,794, filed on May 4, 2016.

(51) Int. Cl.
| | | |
|---|---|---|
| *A61F 5/44* | (2006.01) |
| *A61M 25/00* | (2006.01) |
| *A61B 50/22* | (2016.01) |
| *A61M 39/02* | (2006.01) |

(52) U.S. Cl.
CPC ............ *A61F 5/4405* (2013.01); *A61B 50/22* (2016.02); *A61F 5/4407* (2013.01); *A61M 25/0017* (2013.01); *A61M 2039/0202* (2013.01)

(58) Field of Classification Search
CPC ........ A61F 5/44; A61F 5/4405; A61F 5/4407; A61M 2039/0202; A61M 25/0017; A61B 50/22
See application file for complete search history.

(56) References Cited

U.S. PATENT DOCUMENTS

| | | | |
|---|---|---|---|
| 3,780,736 A | 12/1973 | Chen | |
| 3,965,910 A | 6/1976 | Fischer | |
| 4,306,705 A * | 12/1981 | Svensson | A61B 5/20 251/148 |
| 4,904,245 A | 2/1990 | Chen et al. | |
| 5,312,383 A | 5/1994 | Kubalak | |
| D478,662 S | 8/2003 | Flinchbaugh | |
| 7,780,640 B1 | 8/2010 | Amador | |
| 7,828,269 B2 * | 11/2010 | Iversen | A61F 5/4405 251/319 |
| 7,850,677 B2 | 12/2010 | Blake et al. | |
| 8,684,331 B2 | 4/2014 | Spolski | |
| 8,702,681 B2 | 4/2014 | Douglas et al. | |
| 2007/0213639 A1* | 9/2007 | Salvadori | A61B 5/202 600/584 |
| 2008/0281284 A1 | 11/2008 | Garfield et al. | |
| 2012/0041400 A1* | 2/2012 | Christensen | A61F 5/44 604/318 |
| 2013/0245496 A1 | 9/2013 | Wells et al. | |

FOREIGN PATENT DOCUMENTS

| | | |
|---|---|---|
| JP | 2005052375 | 3/2005 |
| WO | WO 91/01120 | 2/1991 |

* cited by examiner

*Primary Examiner* — Tatyana Zalukaeva
*Assistant Examiner* — Benjamin Klein
(74) *Attorney, Agent, or Firm* — Cislo & Thomas, LLP

(57) ABSTRACT

An improved urine collection bag assembly is presented. The improved urine collection bag assembly of the present invention features a one-way low control valve to prevent the backflow of urine into a urinary catheter a subsequently, into a patient's bladder. The improved urine collection bag also features at a lower end a urine sampling valve. In the exemplary embodiment, the one-way flow control valve is a flap style valve and the sampling valve is a slider style valve.

17 Claims, 7 Drawing Sheets

URINE COLLECTION BAG ASSEMBLY

CLAIM FOR PRIORITY

This application claims priority ti U.S. Provisional Application Ser. No. 62/331,794 entitled "IMPROVED URINE COLLECTION BAG ASSEMBLY," filed on May 4, 2016, the contents of which are incorporated herein in their entirety.

BACKGROUND OF THE INVENTION

Field the Invention

The present invention relates generally to the field of medical devices and more particularly to an improved urine collection bag for the collection and disposal of urine in patients which require urinary tract cauterization, as may be necessary due to a variety of medical coalitions.

Background of the Invention

Normal bladder function includes the cyclic filling of the bladder with urine and periodic voiding when pressure buildup reaches a certain level which may vary within a limited range from patient to patient. The bladder muscles control voiding of the bladder. When healthy, the bladder periodically empties or washes out, allowing bacteria and other potentially harmful micro-organisms to exit the body thus preventing infection.

A variety of medical condition can interfere with the normal function of the bladder. When patients have difficulty urinating, a Foley catheter or other indwelling catheter is often employed to open the bladder allowing the voiding of urine. In typical applications, the catheter is connected or coupled to a urine collection bag, typically through a length of tubing, and urine from the bladder is allowed to drip into the collection bag. When the bag becomes all, a nurse typically applies a clamp to the tubing ahead of the bag, decouples the bag and replaces it with a new bag. After a new beg is attached, the clamp may be removed.

Many problems may arise with catheters and urine collection bags used as described above and, most particularly, catheter associated urinary tract infections. Urinary tract infections are among the most common type of healthcare related infection. Virtually all healthcare related urinary tract infections are caused by the use of instrumentation in the urinary tract. Catheter related urinary tract infections are associated with increased morbidity, hospital costs and length of stay. Urine collection bags are often reservoirs for drug resistant bacteria ad urine backflow from a collection bag is frequently the primary cause of urinary tract infections.

Medical professionals generally believe that the most common cause of urinary tract infections is the backflow of urine into the urinary tract when the urine collection bag is raised above the bladder level. Pathogens may enter the urinary tract by migration from a contaminated collection bag along the internal lumen of the catheter.

Accordingly, there is a need in the art for a urine collection bag that prevents or reduces the possibility of urine backflow into a patient's bladder. Such a bag would dramatically reduce the risk of a urinary tract infection in the patient. Reductions in urinary tract infections would have a positive effect on patient health and would decrease the overall cost of treating patients with urinary tract catheters.

SUMMARY OF THE INVENTION

The present invention improved urine collection bag assembly includes a urine collection bag having an inlet and an outlet, a one-way flow control valve at the inlet and a sampling valve at the outlet. Two embodiments of the urine collection bag assembly are presented. In one embodiment, the one-way flow control valve is mounted at the top of, and just outside of, the urine collection bag and in an alternative embodiment, the one-way flow control valve is mounted on the side of the urine collection bag. In either embodiment, the one-way flow control valve includes an inlet opening which connects via a length of flexible tubing do a urinary catheter and an outlet opening that drains into the urine collection bag.

The sampling valve of the improved urine collection bag assembly is located at a lower end of the urine collection bag. The sampling valve allows for urine samples to be drawn from the bag. The sampling valve is a slide style valve which allows urine to flow from the urine collection bag through an inlet to the sampling valve and through an outlet located at a lower end of the sampling valve. The lower end of the sampling valve includes a threaded connection for the ready attachment of accessories such as urine collection or sampling bottles, as well as the attachment of screw caps when the sampling valve is not in use.

The improved urine collection bag assembly improves upon the prior art by providing a one-way flow control valve in the fluid path between the urine collection bag and a urinary catheter. Therefore, in the event the urine collection bag assembly is elevated above the patient's bladder, urine is prevented from back-flowing from the collection bag, through the catheter and into the patient's bladder.

Optionally, the one-way flow control valve of the collection bag assembly and a catheter connection tube interconnecting the urine collection bag assembly and a urinary catheter may be equipped with antibacterial coatings to further minimize the likelihood that any urine residue that may reside in the catheter connection tube or the one-way flow control valve could cause a urinary tract infection could that residue inadvertently backflow into a patient's bladder.

The above and other features of the invention will become more apparent from the following detailed description.

DETAILED DESCRIPTION OF THE PREFERRED EMBODIMENTS

The present invention will now be described more fully hereinafter with reference to the accompany drawings, in which preferred embodiments of the invention are shown. The invention may, however, may be embodied in many different forms and should not be construed as being limited to the embodiments set forth herein. Rather these embodiments are provided so that this disclosure will be thorough and complete, and will fully convey the scope of the invention to those skilled in the art. Like a numbers refer to like elements throughout.

The urine collection beg assembly 10 of the present invention improves upon the prior art and reduces urinary tract infections by providing a one-way flow control valve 18 in the fluid path between a urine collection bag 12 and a urinary catheter (not shown). Therefore, in the event the urine collection bag assembly 10 is elevated above the level of the patient's bladder, a situation which commonly occurs when urine collection bags are hung from a rack, urine is prevented from back-flowing from the urine collection bag assembly 12, through a catheter and into the patient's bladder.

Figure 1:
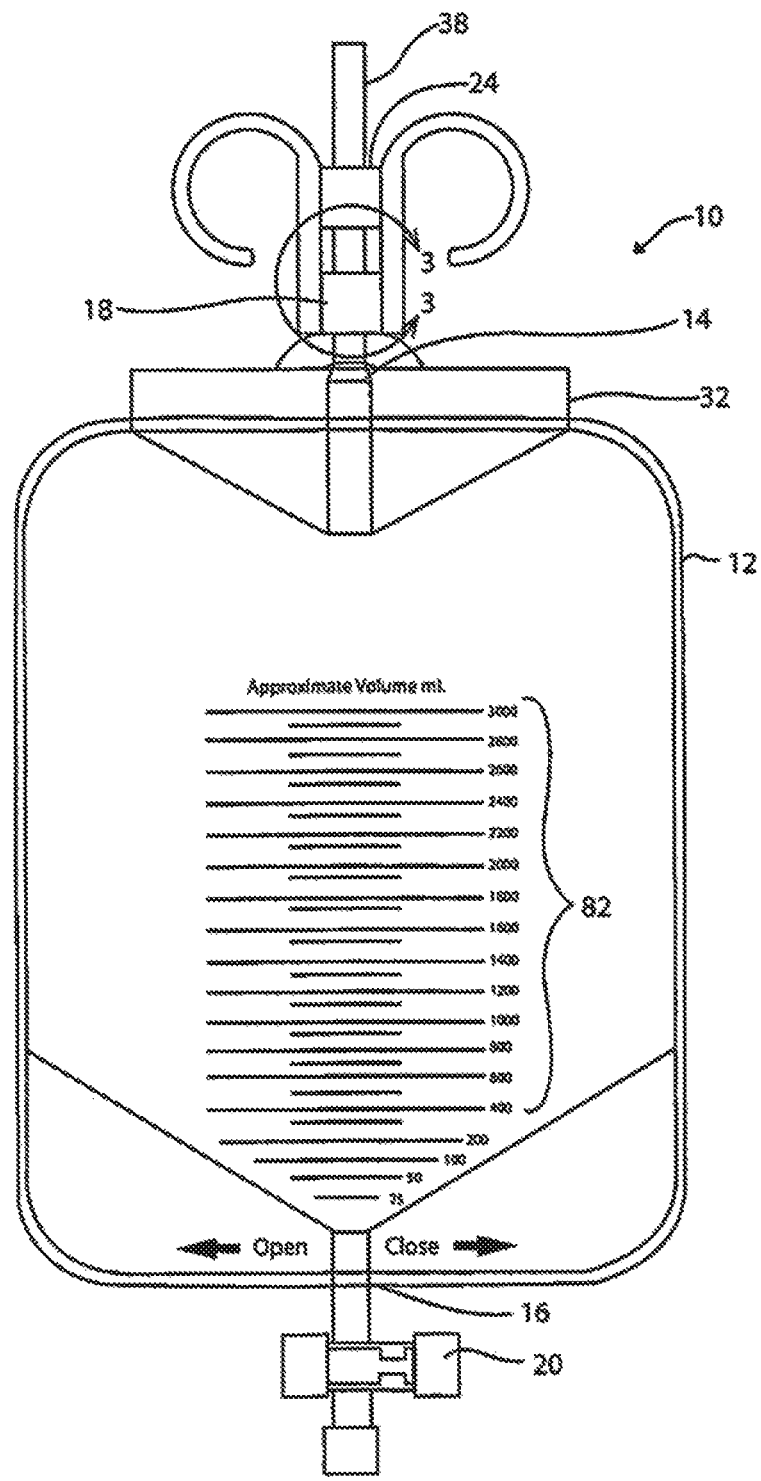
FIG. 1 is a schematic front plan view of an exemplary embodiment of the urine collection bag of the preset invention.
Figure 2:
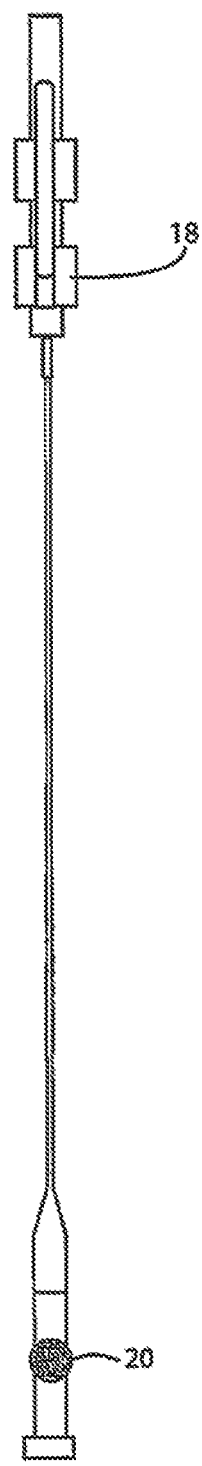
FIG. 2 is a schematic side view of the urine collection beg of FIG. 1.
Figure 3:
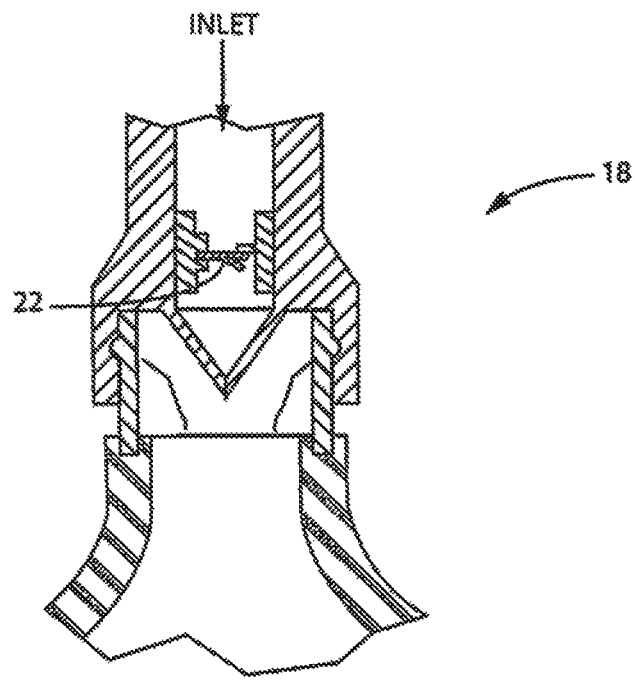
FIG. 3 is a schematic detail view of an exemplary one-way flow control valve suitable for use with the urine collection bag assembly of the present invention.
Figure 4:
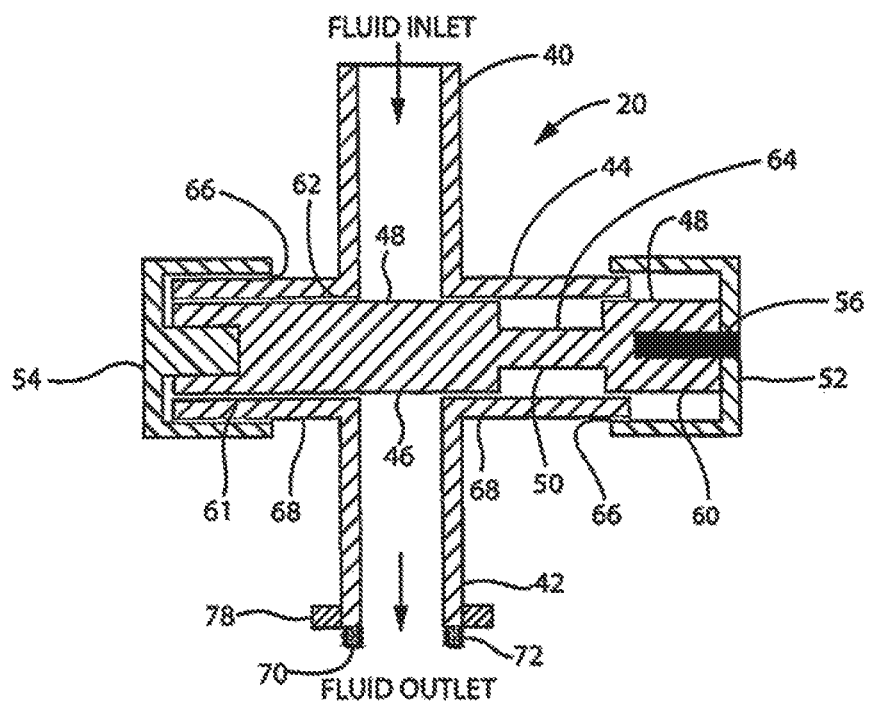
FIG. 4 is a schematic, cross-sectional view of a sampling valve of the present invention.
Figure 5:
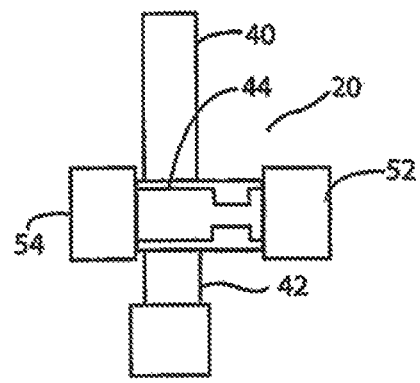
FIG. 5 is a schematic, front view of a sampling valve of the present invention shown in the closed position.
Figure 6:
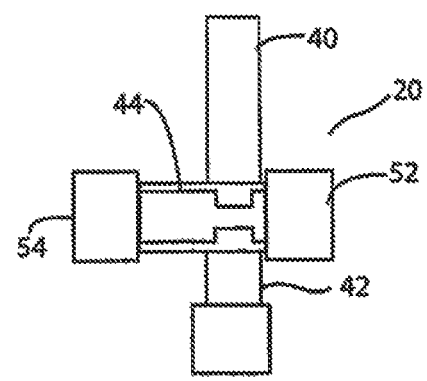
FIG. 6 is a schematic, front view of a sampling valve of the present invention shown in the open position.
Figure 7:
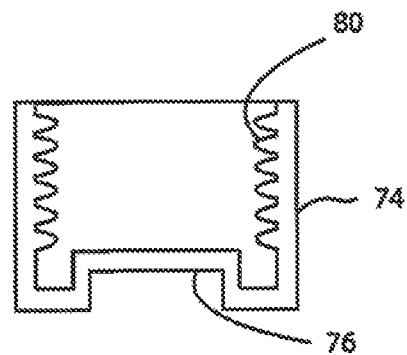
FIG. 7 is a schematic, cross-sectional view of a screw cap suitable for use with the sampling valve assembly of the present invention.

With reference to FIGS. 1-3, the present invention urine collection bag assembly 10 includes the urine collection bag 12 having an upper inlet 14 and a lower outlet 16. The urine collection bag assembly 10 also includes the one-way flow control valve 18 disposed exterior to the urine collection bag and above the upper inlet 14. At the lower outlet 16 of the urine collection bag 12 is located a sampling valve 20 exterior to the urine collection bag and below the lower outlet 16. The one-way flow control valve 18, urine collection bag 12 and sampling valve 20 being in fluid communication.

The one-way flow control valve 18 has an inlet and an outlet, the outlet of the one-way flow control valve 18 being connected to the upper inlet 14 of the urine collection bag 12. The one-way urine flow control valve 18 should present little resistance to fluid flow in one direction and high resistance to fluid flow in an opposite direction. Flap style flow control valves are well suited for use in the urine collection bag assembly of the present invention. Flap style valves incorporate a flexible flap element 22 (see FIG. 3) which opens in one direction in the presence of fluid flow, but closes if a reverse flow condition is experienced. One design for a suitable flap style flow control valve is disclosed in U.S. Pat. No. 7,410,481 entitled "URETHRAL CATHETER DEVICE AND METHOD OF USING," which issued to Cheryl Mitts at al. on Aug. 12, 2008. Several other types of one-way fluid flow control valves including needle valves and check ball style valves are known in the valve design art and may also be suitable for use in with the improved urine collection bag assembly of the present invention.

Figure 8:
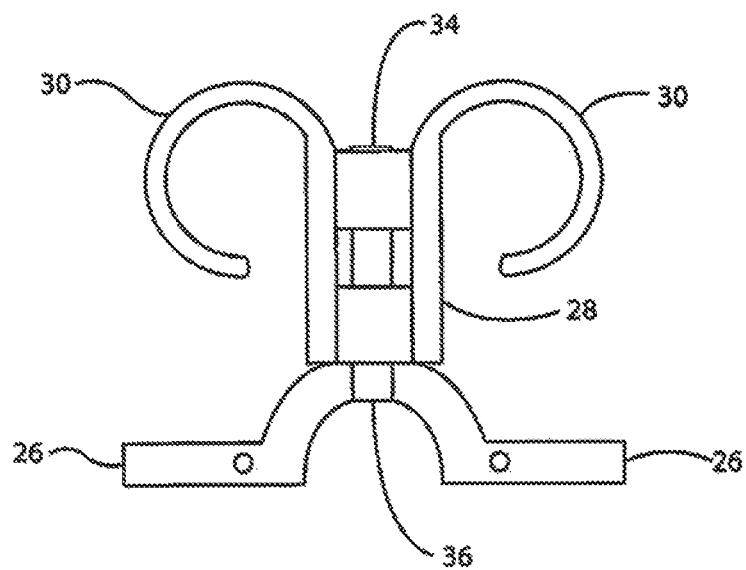
FIG. 8 is a front view a perspective view a rack hanger of the present invention.

With reference to FIGS. 1 and 8, the urine collection bag assembly of the present invention 10 includes an inlet adapter 24. The inlet adapter 24 has an inlet 34 and an outlet 36 and includes legs 26, a valve body portion 28 and curved rack hooks 30. The legs 26 allow the inlet adapt 24 to be attached to a side of an upper end 32 the urine collection bag 12. The valve body portion 28 is adapted to receive the one-way flow control valve 18. The curved books 30 extend from the valve body portion 28 and allow the urine collection bag assembly 10 to be hung from a rack (not shown) which is the standard practice in most hospitals. The inlet end 34 of the inlet adapter 24 is configured to connect to flexible thing 38 (see FIG. 1) which interconnects the urine collection bag assembly 12 with a urinary catheter (not shown). The outlet end 36 of the inlet adapter 24 interconnects via tubing with the inlet 14 of the urine collection bag 12.

With reference to FIGS. 4-7, the sampling valve 20 has a vertical, hollow cylindrical valve inlet portion 40 and a vertical, hollow cylindrical valve outlet portion 42. The vertical, hollow cylindrical inlet and outlet portions 40 and 42 being in fluid communication. Disposed between the sampling valve inlet portion 40 and the sampling valve outlet portion 42 is a horizontal, hollow cylindrical slide passageway 44. Disposed within the slide passageway 44 is a valve slider 46. The valve slider 46 has right and left cylindrical and portions 60 and 61 which have an outside diameter 48 which is configured to be a tight slip fit or friction fit with an inside diameter 62 of the hollow cylindrical slide passageway 44. The fit between the inside diameter 62 of the slide passageway 44 and outside diameter 48 of the right and left cylindrical end portions 60 and 61 of the valve slider 46 should be watertight. When either of the right or left cylindrical end portions 60 and 61 are disposed between the vertical, hollow cylindrical inlet and outlet portions 40 and 42, fluid communication between portions 40 and 42 is cutoff.

Disposed between the end portions 60 and 61 of the valve slider 46 is a cylindrical intermediate portion 50. The cylindrical intermediate portion 50 has an outside diameter 64 substantially smaller than that of the slide passageway 44 such that urine will freely flow through the vertical, hollow cylindrical valve inlet and outlet portions 40 and 42, when the intermediate portion 50 of the valve slider 46 is moved to a position between the hollow cylindrical valve inlet and outlet portions 40 and 42.

Secured to the right end portion 61 of the valve slider 44 is a right end cap 52 and secured to the left end portion 60 of the valve slider 44 is a left end cap 54. The right and left end caps 52 and 54 are configured to have an inside diameter 66 which allows the right and left end caps 52 and 54 to freely slide over an outside diameter 68 of the slide passageway 44. The dimensions of the right and left end portions 60 and 61 and right and left end caps 52 and 54 are configured such that when the left end cap 54 is pushed fully to the right, the sampling valve 20 is in a closed position. (See FIG. 5.) Similarly, when the right end cap 52 is pushed fully to the left, the sampling valve 20 is in an open position. (See FIG. 6.)

The right and left screw caps 52 and 54 may be attached to the right and left end portions by a number of means. For example, in FIG. 4, the left screw cap 54 is press fit and then glued s the end portion 61, whereas the right screw cap 52 is pinned and glued to the right end portion 61 via a pin 56.

Disposed at a lower end 70 of the hollow cylindrical valve outlet portion 42 are screw threads 72. The screw threads 72 allow for the ready attachment of accessories with mating threads 80 such as urine sampling bottles (not shown) or a screw cap 74 (see FIG. 7) when the sampling valve 20 is not in use. The screw cap 74 is equipped with a cylindrical inset 76 that engages and seals the lower end 70 of hollow cylindrical valve outlet portion 42. The lower end 70 of hollow cylindrical valve outlet portion 42 is also equipped with a ledge 78 which acts as positive stop for the screw cap 74.

The urine collection beg 12 will typically be made by heat sealing or otherwise securing flexible, precut flat sheets of a biologically inert plastic material to form a beg having an internal volume. Suitable materials for the urine collection bag 12 include polyvinyl chloride, polyethylene and polypropylene. Other materials may also be suitable. The urine collection bag 12 would also typically be printed with folly graduated volume measurements 82 (see FIG. 1.). Typical dimensions for the urine collection bag 12 are a width approximately 22 centimeters and a height of approximately 30 centimeters. The urine collection bag 12 will typically have a volume of about 3000 milliliters.

Similarly, the one-way flow control valve 18 and sampling valve 20 will typically be made of an injection moldable biologically inert plastic material. Polyethylene and polypropylene are two such suitable materials, which are known in the art. Other plastic materials, such as polyvinyl chloride a also suitable.

The one-way flow control valve 18 of the collection bag 12 and a catheter collection tube 38 interconnecting the urine collection bag assembly 10 and a urinary catheter (not shown) may be equipped with antibacterial coatings to further minimize the likelihood that any urine drips that may reside in the catheter connection tube 38 or the one-way flow control valve 18 would cause a urinary tract infection.

Figure 9:
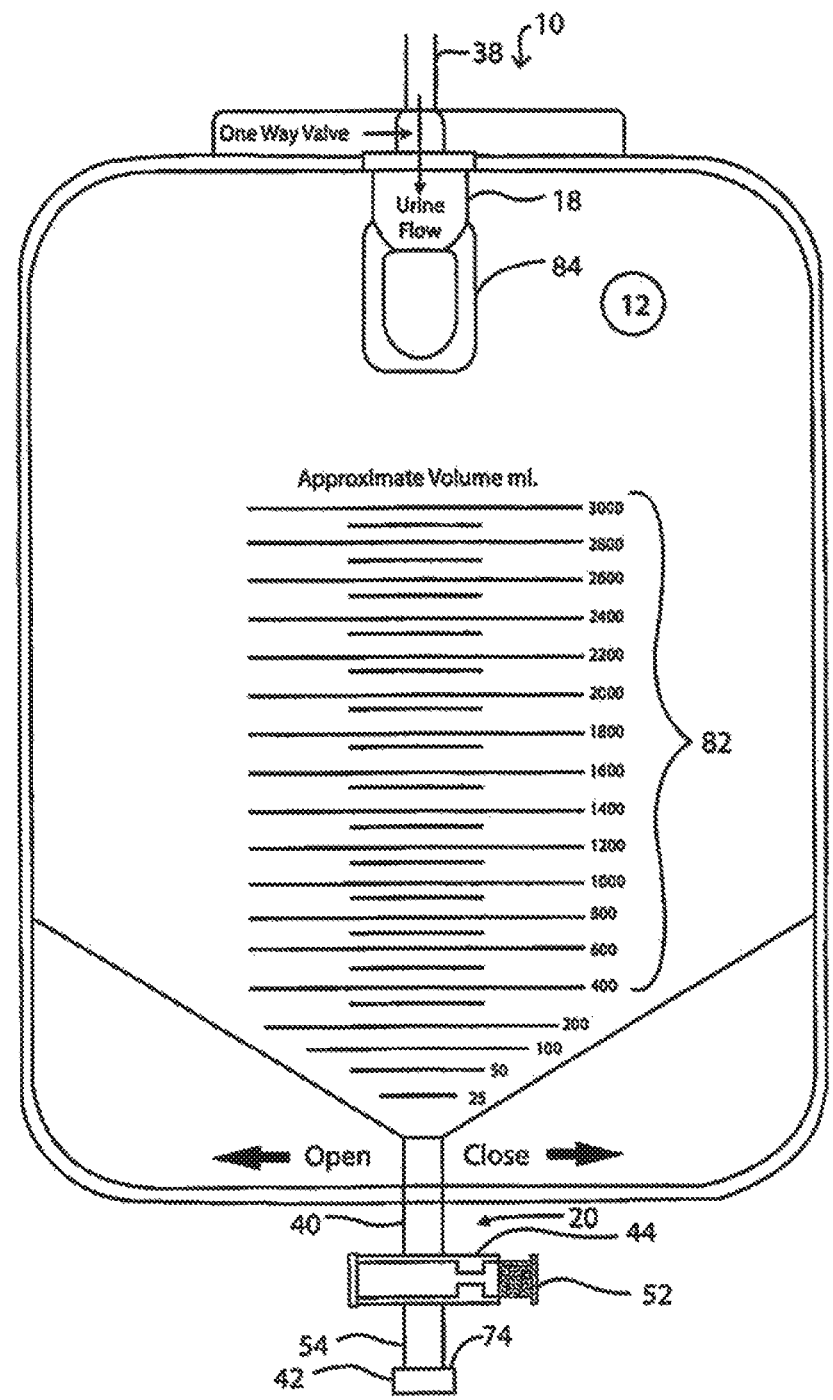
FIG. 9 is a schematic front plan view of an alternative embodiment of the urine collection bag of the present invention.
Figure 10:
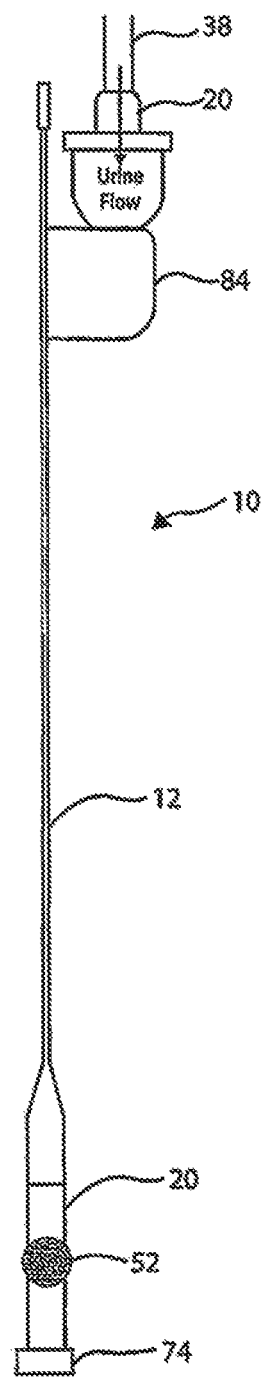
FIG. 10 is a schematic side view of the alternative embodiment of the urine collection bag of FIG. 1.

With reference to FIG. 9-10, an alternative embodiment of the urine collection bag assembly of the present invention is shown. Like the first embodiment, this alternative embodiment includes a urine collection bag 12, a one-way flow control valve 18 disposed near the top of the urine collection bag 12 and a sampling valve 20 disposed at a bottom of the urine collection bag 12. In this embodiment, the one-way flow control valve 20 includes an integral urine drip container 84 and the integral flow control valve and drip container are mounted to a side of the urine collection bag 12, rather than exterior to the bag. Otherwise, the construction details are the same as for the principal embodiment.

The invention claimed is:

1. A urine collection bag assembly comprising:
a urine collection bag having an inlet and an outlet;
a one-way flow control valve disposed above and exterior to the inlet of the urine collection bag, the one way flow control valve having an inlet and an outlet, the outlet of the one-way flow control valve connected to the inlet of the urine collection bag; the inlet of the one-way flow control valve being attachable to a urinary catheter, wherein the one-way flow control valve prevents the backflow of urine out of the urine collection bag;
a sampling valve disposed below and exterior to the inlet of the urine collection bag, the sampling valve having an inlet and an outlet, the inlet of the sampling valve connected to the outlet of the urine collection bag;
wherein, the sampling valve comprises:
vertically oriented, hollow cylindrical inlet and outlet portions, the vertically oriented, hollow cylindrical inlet and outlet portions being in fluid communication;
a horizontally oriented, cylindrical passageway portion disposed between the vertically oriented hollow cylindrical inlet and outlet portions;
a cylindrical sliding element disposed within the passageway portion, the cylindrical sliding element including cylindrical end portions wherein the cylindrical end portions prevent fluid communication between the vertically oriented, hollow cylindrical inlet and outlet portions when disposed between the vertically oriented, hollow cylindrical inlet and outlet portions;
the cylindrical sliding element having an intermediate portion disposed between the cylindrical end portions, wherein the intermediate portion allows fluid communication between the vertically oriented, hollow cylindrical inlet and outlet portions when the intermediate portion is disposed between the vertically oriented, hollow cylindrical inlet and outlet portions;
wherein the sampling valve further comprises cylindrical end caps having an inside diameter and a depth, the cylindrical end caps being affixed to the cylindrical end portions of the cylindrical sliding element, the inside diameter of the cylindrical end caps being configured to be larger than an outside diameter of the horizontally oriented, cylindrical passageway portion, wherein the cylindrical end caps may slide along an exterior of the horizontally oriented, cylindrical passageway portion for the duration of their depths; and
curved hooks extending upwardly from a top of the urine collection bag wherein the curved hooks allow the urine collection bag to be hung from a rack.

2. A urine collection bag assembly comprising:
a urine collection bag having an inlet and an outlet;
a one-way flow control valve having an inlet and an outlet, the outlet of the one-way flow control valve connected to the inlet of the urine collection bag; the inlet of the one-way flow control valve being attachable to a urinary catheter, wherein the one-way flow control valve prevents the backflow of urine out of the urine collection bag;
wherein, the one-way flow control valve is disposed above and exterior to the inlet of the urine collection bag;
a sampling valve having an inlet and an outlet, the inlet of the sampling valve connected to the outlet of the urine collection bag;
wherein the sampling valve comprises:
vertically oriented, hollow cylindrical inlet and outlet portions, the vertically oriented, hollow cylindrical inlet and outlet portions being in fluid communication;
a horizontally oriented, cylindrical passageway portion disposed between the vertically oriented hollow cylindrical inlet and outlet portions;
a cylindrical sliding element disposed within the passageway portion, the cylindrical sliding element including cylindrical end portions wherein the cylindrical end portions prevent fluid communication between the vertically oriented, hollow cylindrical inlet and outlet portions when disposed between the vertically oriented, hollow cylindrical inlet and outlet portions;
the cylindrical sliding element having an intermediate portion disposed between the cylindrical end portions, wherein the intermediate portion allows fluid communication between the vertically oriented, hollow cylindrical inlet and outlet portions when the intermediate portion is disposed between the vertically oriented, hollow cylindrical inlet and outlet portions; and
wherein the sampling valve further comprises cylindrical end caps having an inside diameter and a depth, the cylindrical end caps being affixed to the cylindrical end portions of the cylindrical sliding element, the inside diameter of the cylindrical end caps being configured to be larger than an outside diameter of the horizontally oriented, cylindrical passageway portion, wherein the cylindrical end caps may slide along an exterior of the horizontally oriented, cylindrical passageway portion for the duration of their depths.

3. The urine collection bag assembly of claim 2, wherein the one-way flow control valve is selected from the group consisting of flap, needle, and check ball style valves.

4. The urine collection bag assembly of claim 2, wherein the cylindrical end caps, the cylindrical sliding element and the horizontally oriented, cylindrical passageway portion are configured such that when one cylindrical end cap is pressed to the extent of its depth, fluid communication between the vertically oriented, hollow cylindrical inlet and outlet portions is prevented and when the other cylindrical end cap is pressed to the extent of its depth, fluid communication between the vertically oriented, hollow cylindrical inlet and outlet portions is allowed.

5. The urine collection bag assembly of claim 2, wherein the outlet of the sampling valve is threaded to threadably engage accessories.

6. The urine collection bag assembly of claim 5, wherein one of the accessories is a cap, the cap having a raised inset which seals the outlet of the sampling valve when engaged.

7. The urine collection bag assembly of claim 2, wherein the collection bag includes a graduated volume scale.

8. The urine collection bag assembly of claim 2, further including a catheter connection tube wherein the catheter connection tube interconnects the inlet of the one-way flow control valve with a urinary catheter.

9. The urine collection bag assembly of claim 2, wherein the urine collection bag, one-way flow control valve and sampling valve are made from biologically inert materials.

10. The urine collection bag assembly of claim 9, wherein the urine collection bag, one-way flow control valve, and sampling valve each comprise one or more materials selected from the group consisting of polypropylene, polyethylene and poly vinyl chloride.

11. A urine collection bag assembly comprising:
a urine collection bag having an inlet and an outlet;
a one-way flow control valve having an inlet and an outlet, the outlet of the one-way flow control valve connected to the inlet of the urine collection bag; the inlet of the one-way flow control valve being attachable to a urinary catheter, wherein the one-way flow control valve prevents the backflow of urine out of the urine collection bag;
a sampling valve having an inlet and an outlet, the inlet of the sampling valve connected to the outlet of the urine collection bag;
wherein, the sampling valve comprises:
vertically oriented, hollow cylindrical inlet and outlet portions, the vertically oriented, hollow cylindrical inlet and outlet portions being in fluid communication;
a horizontally oriented, cylindrical passageway portion disposed between the vertically oriented hollow cylindrical inlet and outlet portions;
a cylindrical sliding element disposed within the passageway portion, the cylindrical sliding element including cylindrical end portions wherein the cylindrical end portions prevent fluid communication between the vertically oriented, hollow cylindrical inlet and outlet portions when disposed between the vertically oriented, hollow cylindrical inlet and outlet portions;
the cylindrical sliding element having an intermediate portion disposed between the cylindrical end portions, wherein the intermediate portion allows fluid communication between the vertically oriented, hollow cylindrical inlet and outlet portions when the intermediate portion is disposed between the vertically oriented, hollow cylindrical inlet and outlet portions and
wherein the sampling valve further comprises cylindrical end caps having an inside diameter and a depth, the cylindrical end caps being affixed to the cylindrical end portions of the cylindrical sliding element, the inside diameter of the cylindrical end caps being configured to be larger than an outside diameter of the horizontally oriented, cylindrical passageway portion, wherein the cylindrical end caps may slide along an exterior of the horizontally oriented, cylindrical passageway portion for the duration of their depths.

12. The urine collection bag assembly of claim 11, wherein the one-way flow control valve is disposed above and exterior to the inlet of the urine collection bag.

13. The urine collection bag assembly of claim 11, wherein the one-way flow control valve is disposed on the side of the urine collection bag.

14. The urine collection bag assembly of claim 11, wherein the one-way flow control valve is selected from the group consisting of flap, needle, and check ball style valves.

15. The urine collection bag assembly of claim 11, wherein the collection bag includes a graduated volume scale.

16. The urine collection bag assembly of claim 11, wherein the end caps, the sliding portion and the horizontally oriented, cylindrical passageway portion are configured such that when one cylindrical end cap is pressed to the extent of its depth, fluid communication between the vertically oriented, hollow cylindrical inlet and outlet portions is prevented and when the other cylindrical end cap is pressed to the extent of its depth, fluid communication between the vertically oriented, hollow cylindrical inlet and outlet portions is allowed.

17. The urine collection bag assembly of claim 11, wherein the outlet of the sampling valve is thread to engage a cap, the cap having a raised inset which seals the outlet of the sampling valve when engaged.

* * * * *